US012681569B2

(12) United States Patent
Zhao et al.

(10) Patent No.: US 12,681,569 B2
(45) Date of Patent: Jul. 14, 2026

(54) HUMAN-COMPUTER INTERACTION USER EXPERIENCE EVALUATION AND OPTIMIZATION METHOD AND SYSTEM, AND STORAGE MEDIUM

(71) Applicant: KINGFAR INTERNATIONAL INC., Beijing (CN)

(72) Inventors: Qichao Zhao, Beijing (CN); Qingju Wang, Beijing (CN)

(73) Assignee: KINGFAR INTERNATIONAL INC., Beijing (CN)

( * ) Notice: Subject to any disclaimer, the term of this patent is extended or adjusted under 35 U.S.C. 154(b) by 0 days.

(21) Appl. No.: 18/970,970

(22) Filed: Dec. 6, 2024

(65) Prior Publication Data

US 2025/0165067 A1 May 22, 2025

Related U.S. Application Data

(63) Continuation of application No. PCT/CN2023/141700, filed on Dec. 25, 2023.

(30) Foreign Application Priority Data

Dec. 30, 2022 (CN) .......................... 202211729030.7

(51) Int. Cl.
G06F 3/01 (2006.01)
A61B 5/16 (2006.01)
(Continued)

(52) U.S. Cl.
CPC .............. *G06F 3/013* (2013.01); *A61B 5/165* (2013.01); *G06F 3/015* (2013.01); *G06N 20/00* (2019.01);
(Continued)

(58) Field of Classification Search
None
See application file for complete search history.

(56) References Cited

U.S. PATENT DOCUMENTS

2020/0104670 A1* 4/2020 Seo ...................... G06V 10/764
2021/0113129 A1* 4/2021 Huang ................... A61B 5/486
(Continued)

FOREIGN PATENT DOCUMENTS

CN 112259237 A 1/2021
CN 112541668 A 3/2021
(Continued)

OTHER PUBLICATIONS

International Search Report dated May 31, 2024 in International Application No. PCT/CN2023/141700. English translation attached.
(Continued)

*Primary Examiner* — Joseph R Haley

(57) ABSTRACT

A method for evaluating and optimizing user experience in human-computer interaction includes: acquiring a multimodal biological signal of a user during human-computer interaction, and preprocessing the multimodal biological signal to extract a fixation position and index parameters of multiple dimensions; standardizing the index parameters, and performing, based on each index parameter and a weight for each index parameter, weighted average to calculate a user experience evaluation score of each dimension; acquiring a weight for the user experience evaluation score, and performing weighted average to calculate an overall user experience evaluation result; visually presenting, based on the overall user experience evaluation result, user experience situation data of the user for a current fixation position; and acquiring a correction parameter of the user, and optimizing, based on the correction parameter, the weights using a machine learning optimization algorithm.

18 Claims, 3 Drawing Sheets

(51) Int. Cl.
     *G06N 20/00*          (2019.01)
     *G06T 11/10*          (2026.01)
(52) U.S. Cl.
     CPC .......... *G06T 11/10* (2026.01); *G06T 2200/24*
                    (2013.01); *G06T 2210/62* (2013.01)

(56)                    References Cited

U.S. PATENT DOCUMENTS

| | | | | |
|---|---|---|---|---|
| 2024/0164677 A1* | 5/2024 | Yildiz | .................... | A61B 5/168 |
| 2025/0216934 A1* | 7/2025 | Kim | ....................... | G06V 20/46 |

FOREIGN PATENT DOCUMENTS

| | | | |
|---|---|---|---|
| CN | 113360371 A | 9/2021 |
| CN | 114816060 A | 7/2022 |
| CN | 116880936 A | 10/2023 |
| EP | 4099250 A1 | 12/2022 |
| WO | 2019139447 A1 | 7/2019 |

OTHER PUBLICATIONS

The Grant Notice from corresponding Chinese Application No. 202211729030.7, dated May 20, 2024. English translation attached.

\* cited by examiner

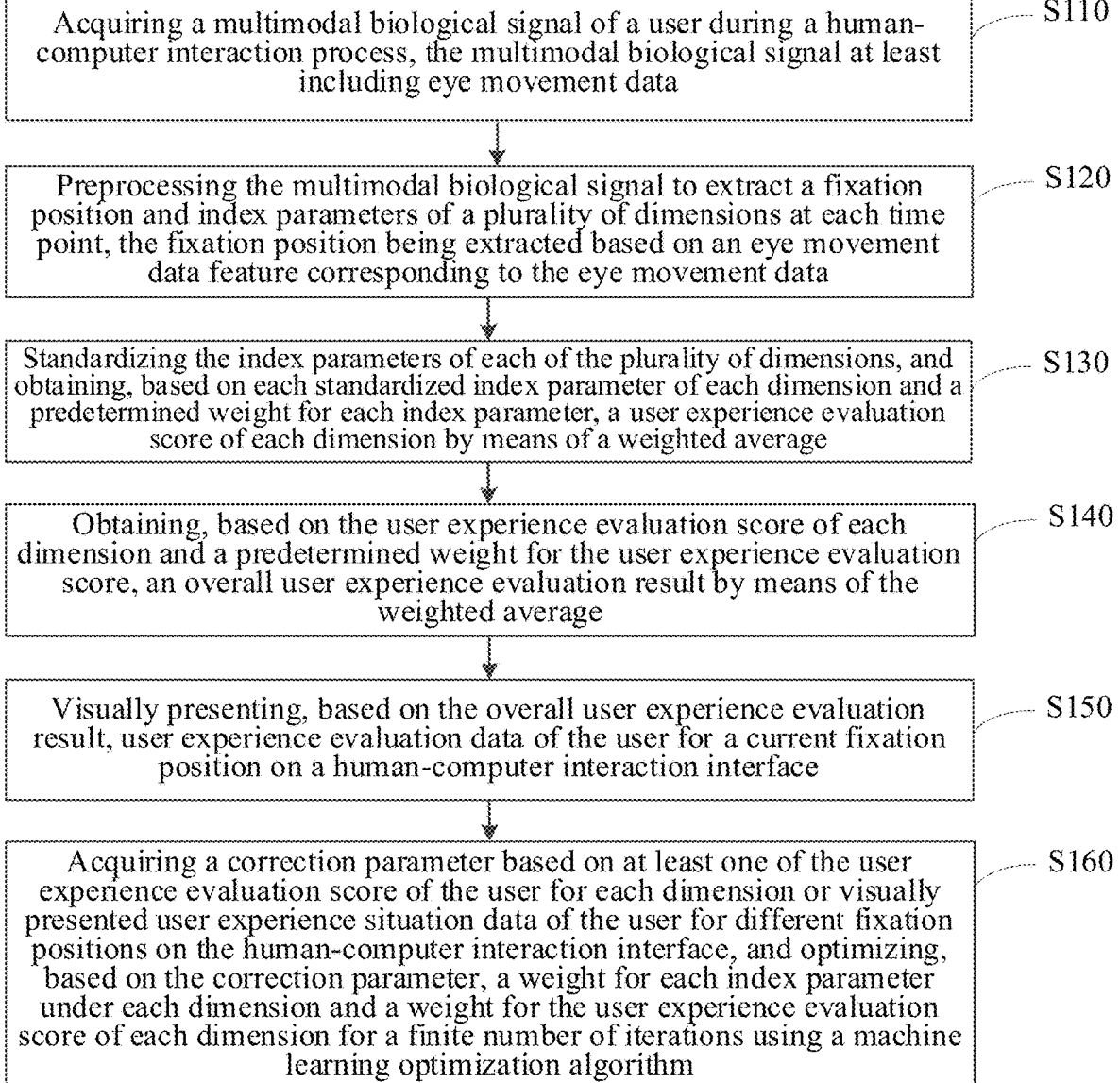

Acquiring a multimodal biological signal of a user during a human-computer interaction process, the multimodal biological signal at least including eye movement data — S110

Preprocessing the multimodal biological signal to extract a fixation position and index parameters of a plurality of dimensions at each time point, the fixation position being extracted based on an eye movement data feature corresponding to the eye movement data — S120

Standardizing the index parameters of each of the plurality of dimensions, and obtaining, based on each standardized index parameter of each dimension and a predetermined weight for each index parameter, a user experience evaluation score of each dimension by means of a weighted average — S130

Obtaining, based on the user experience evaluation score of each dimension and a predetermined weight for the user experience evaluation score, an overall user experience evaluation result by means of the weighted average — S140

Visually presenting, based on the overall user experience evaluation result, user experience evaluation data of the user for a current fixation position on a human-computer interaction interface — S150

Acquiring a correction parameter based on at least one of the user experience evaluation score of the user for each dimension or visually presented user experience situation data of the user for different fixation positions on the human-computer interaction interface, and optimizing, based on the correction parameter, a weight for each index parameter under each dimension and a weight for the user experience evaluation score of each dimension for a finite number of iterations using a machine learning optimization algorithm — S160

FIG. 1

HUMAN-COMPUTER INTERACTION USER EXPERIENCE EVALUATION AND OPTIMIZATION METHOD AND SYSTEM, AND STORAGE MEDIUM

CROSS-REFERENCE TO RELATED APPLICATION

The present application is a continuation of International Patent Application No. PCT/CN2023/141700, filed on Dec. 25, 2023, which claims priority to Chinese Patent Application No. 202211729030.7, titled "METHOD AND SYSTEM FOR EVALUATING AND OPTIMIZING USER EXPERIENCE IN HUMAN-COMPUTER INTERACTION, AND STORAGE MEDIUM", and filed with China National Intellectual Property Administration on Dec. 30, 2022, both of which are incorporated herein by reference in their entireties.

FIELD

The present disclosure relates to the field of ergonomics and user experience recognition technologies, and more particularly, to a method and a system for evaluating and optimizing user experience in human-computer interaction, and a storage medium.

BACKGROUND

Ergonomics is an interdisciplinary subject that studies an interaction among humans, machines, and an environment. In a user experience evaluation of ergonomics, user emotion recognition (i.e. user experience evaluation) is a very important dimension to be considered. In addition to a subjective report, physiological measurement is also an objective and effective emotion recognition method.

A traditional emotion recognition method based on physiological measurement mostly uses audio data or video data to recognize an emotional state of a target object. In this method, it is difficult to accurately analyze obtained data type on the one hand, and a large amount of data processing and analysis is required on the other hand. Thus, application of this method in user experience evaluation practice is limited. In addition, due to the limitation of the amount of calculation, this method cannot achieve real-time recognition and feedback.

For this reason, how to provide a method and system for automatically and real-timely evaluating user experience in a human-computer interaction process based on richer data is an urgent problem to be solved.

SUMMARY

In view of this, embodiments of the present disclosure provide a method and a system for evaluating and optimizing user experience in human-computer interaction, and a storage medium to eliminate or improve one or more defects existing in the traditional technology.

An aspect of the present disclosure provides a method for evaluating and optimizing user experience in human-computer interaction. The method includes: acquiring a multimodal biological signal of a user during a human-computer interaction process, the multimodal biological signal at least including eye movement data; preprocessing the multimodal biological signal to extract a fixation position and index parameters of a plurality of dimensions at each time point, the fixation position being extracted based on an eye movement data feature corresponding to the eye movement data; standardizing the index parameters of each of the plurality of dimensions, and obtaining, based on each standardized index parameter of each dimension and a predetermined weight for each index parameter, a user experience evaluation score of each dimension by means of a weighted average; obtaining, based on the user experience evaluation score of each dimension and a predetermined weight for the user experience evaluation score, an overall user experience evaluation result by means of the weighted average; visually presenting, based on the overall user experience evaluation result, user experience situation data of the user for a current fixation position on a human-computer interaction interface; and acquiring a correction parameter based on at least one of the user experience evaluation score of the user for each dimension or the visually presented user experience situation data of the user for different fixation positions on the human-computer interaction interface, and optimizing, based on the correction parameter, a weight for each index parameter of each dimension and a weight for the user experience evaluation score of each dimension for a finite number of iterations using a machine learning optimization algorithm.

In some embodiments of the present disclosure, the multimodal biological signal further includes one or a combination of physiological data, electroencephalographic data, brain imaging data, or behavioral data; and the plurality of dimensions at least includes one or a combination of a fatigue degree dimension, an emotional state dimension, or a cognitive load dimension.

In some embodiments of the present disclosure, the preprocessing the multimodal biological signal to extract the fixation position and the index parameters of the plurality of dimensions at each time point includes: extracting, based on the eye movement data feature, a plurality of index parameters including fixation position, blink rate, and eyelid closure; extracting, based on a corresponding physiological data feature, a plurality of index parameters including a serum creatinine SCR amplitude and an LF/HF value of a frequency-domain index, where LF represents a low-frequency radiofrequency, and HF represents a high-frequency radiofrequency; and extracting, based on a corresponding brain imaging data feature, a plurality of index parameters including an alpha asymmetry index, an $(\alpha+\theta)/\beta$ value of a frequency-domain index, and oxyhemoglobin saturation HbO2, where $\alpha$, $\beta$, and $\theta$ represent a signal quantity within a given frequency band of an $\alpha$ wave, a signal quantity within a given frequency band of a $\beta$ wave, and a signal quantity within a given frequency band of a $\theta$ wave, respectively.

In some embodiments of the present disclosure, the obtaining, based on each standardized index parameter of each dimension and the predetermined weight for each index parameter, the user experience evaluation score of each dimension by means of the weighted average includes: calculating, based on the blink rate and the eyelid closure and weights corresponding to the index parameters of the blink frequency and the eyelid closure, a user experience evaluation score of the fatigue degree dimension by means of the weighted average; calculating, based on the serum creatinine SCR amplitude and the LF/HF value of the frequency-domain index and weights corresponding to the index parameters of the serum creatinine SCR amplitude and the LF/HF value of the frequency-domain index, a user experience evaluation score of the emotional state dimension by means of the weighted average; and calculating a user experience evaluation score of the cognitive load dimension by means of the weighted average and based on the alpha asymmetry index, the $(\alpha+\theta)/\beta$ value of the frequency-domain index, the oxyhemoglobin saturation $HbO2$, and weights corresponding to the index parameters of the alpha asymmetry index, the $(\alpha+\theta)/\beta$ value of the frequency-domain index, and the oxyhemoglobin saturation $HbO2$.

In some embodiments of the present disclosure, values of the standardized index parameters include a positive value and a negative value; and the method for evaluating and optimizing user experience in human-computer interaction further includes: normalizing the standardized index parameters of the plurality of dimensions, values of the normalized index parameters of the plurality of dimensions including a positive value and a negative value.

In some embodiments of the present disclosure, the machine learning optimization algorithm is a Newton method or a gradient descent method; and the optimizing, based on the correction parameter, the weight for each index parameter of each dimension and the weight for the user experience evaluation score of each dimension for the finite number of iterations using the machine learning optimization algorithm includes: building a machine learning optimization model by taking the weight for each index parameter of each dimension and the weight for the user experience evaluation score of each dimension as to-be-optimized parameters; constructing a loss function based on the correction parameter; and optimizing the machine learning optimization model for the finite number of iterations based on the loss function, and obtaining the optimized weight for each index parameter of each dimension and the optimized weight for the user experience evaluation score of each dimension.

In some embodiments of the present disclosure, the visually presenting, based on the overall user experience evaluation result, the user experience situation data of the user for the current fixation position on the human-computer interaction interface includes: labeling at least one of different colors or transparency levels for the current fixation location based on the overall user experience evaluation result.

In some embodiments of the present disclosure, the acquiring the correction parameter based on the at least one of the user experience evaluation score of the user for each dimension or the visually presented user experience situation data of the user for the different fixation positions on the human-computer interaction interface includes: acquiring subjective questionnaire data of the user for a fatigue degree dimension, an emotional state dimension, and a cognitive load dimension, and calculating the correction parameter based on the subjective questionnaire data.

In some embodiments of the present disclosure, the acquiring the correction parameter based on the at least one of the user experience evaluation score of the user for each dimension or the visually presented user experience situation data of the user for the different fixation positions on the human-computer interaction interface further includes: acquiring a subjective score of the user for the visually presented user experience situation of the different fixation positions on the human-computer interaction interface, and calculating the correction parameter based on the subjective score.

In some embodiments of the present disclosure, the method for evaluating and optimizing user experience in human-computer interaction further includes: labeling, based on fixation positions at a plurality of historical time points and overall user experience evaluation results corresponding to the fixation positions, at least one of different colors or transparency levels for the different fixation positions on the human-computer interaction interface, and filling a blank region based on at least one of a color or transparency level of a fixation position around the blank region, to visually present the user experience situation data of the user for different regions on the human-computer interaction interface.

In some embodiments of the present disclosure, the method for evaluating and optimizing user experience in human-computer interaction further includes: generating a user experience feedback report based on the visually presented user experience situation data of the user for the current fixation position on the human-computer interaction interface, the user experience feedback report including user experience feedback reports generated for different partitions based on predetermined partitions on the human-computer interaction interface.

Another aspect of the present disclosure provides a system for evaluating and optimizing user experience in human-computer interaction. The system includes a processor and a memory having computer instructions stored therein. The processor is configured to execute the computer instructions stored in the memory. The system, when the computer instructions are executed by the processor, implements the method for evaluating and optimizing user experience in human-computer interaction as described in any one of the above embodiments.

Yet another aspect of the present disclosure provides a computer-readable storage medium. The computer-readable storage medium has a computer program stored thereon. The computer program, when executed by a processor, implements the method for evaluating and optimizing user experience in human-computer interaction as described in any one of the above embodiments.

In the method and system for evaluating and optimizing user experience in human-computer interaction and the storage medium according to the present disclosure, the fixation position and the index parameters of the plurality of dimensions can be extracted based on the multimodal biological signal feature; the weighted calculation is performed based on the index parameters of the plurality of dimensions to obtain the objective and accurate user experience evaluation result, and the fixation position is associated with the user experience evaluation result; the experience situation of the user for different regions on the human-computer interaction interface can be further obtained; and the user experience in the human-computer interaction can be automatically and real-timely evaluated based on the richer data.

Additional advantages, purposes, and features of the present disclosure will be set forth in part in the following description, or will become apparent in part to those skilled in the related art after studying hereinafter, or can be learned from the practice of the present disclosure. The purposes and other advantages of the present disclosure can be achieved and obtained by structures specifically pointed out in the specification and the drawings.

Those skilled in the related art will understand that purposes and advantages that can be achieved with the present disclosure are not limited to those in the above specific description, and the above and other purposes that can be achieved with the present disclosure will be more clearly understood based on the following detailed description.

BRIEF DESCRIPTION OF THE DRAWINGS

The drawings described herein are used to provide a further understanding of the present disclosure, constitute a part of the present disclosure, and do not constitute a limitation of the present disclosure.

FIG. 1 is a schematic diagram of a method for evaluating and optimizing user experience in human-computer interaction according to an embodiment of the present disclosure.

DETAILED DESCRIPTION OF THE EMBODIMENTS

Figure 2:
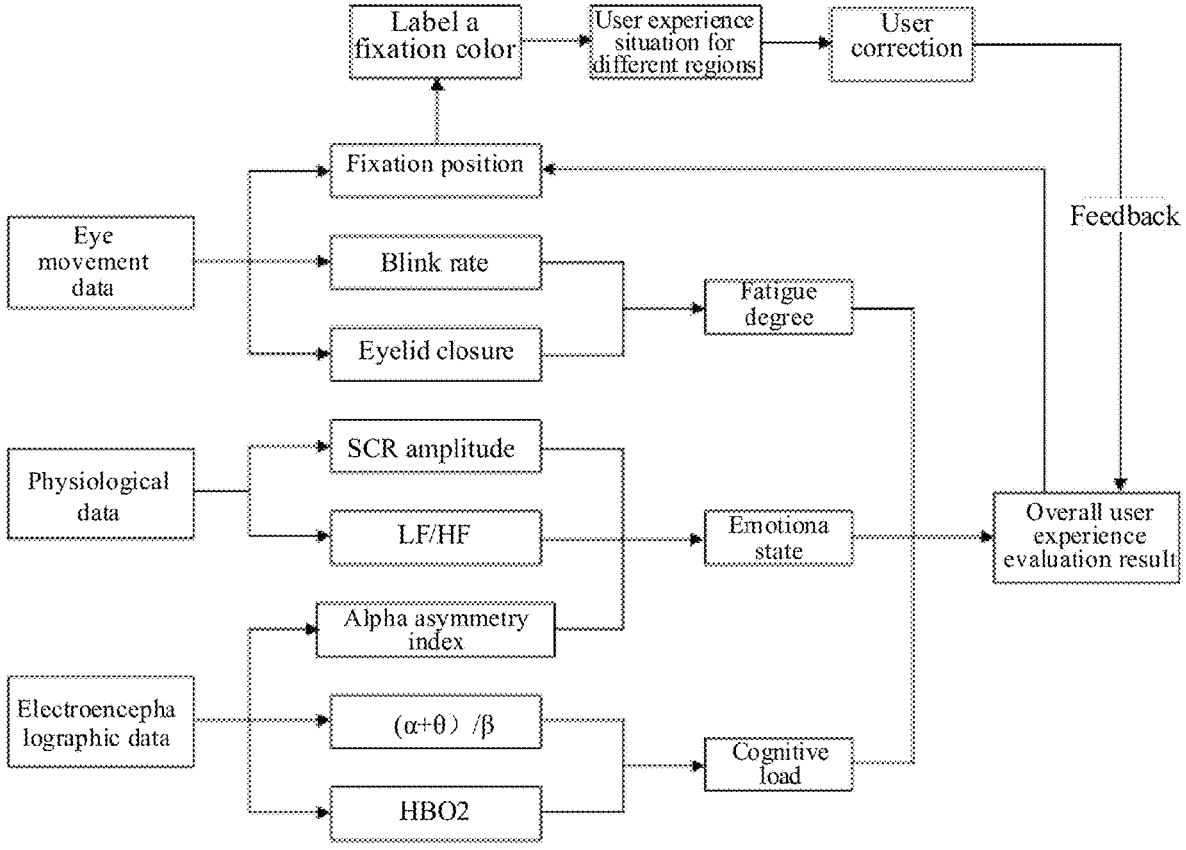
FIG. 2 is a flowchart of a method for evaluating and optimizing user experience in human-computer interaction according to an embodiment of the present disclosure.

In order to make purposes, technical solutions, and advantages of the present disclosure clearer, the present disclosure is further described in detail in combination with embodiments and the accompanying drawings. Herein, exemplary embodiments of the present disclosure and description thereof are used to explain the present disclosure, but are not intended to be a limitation on the present disclosure.

Herein, it should also be noted that in order to avoid blurring the present disclosure due to unnecessary details, only structures and/or processing steps closely related to the solutions of the present disclosure are shown in the accompanying drawings, while other details that have little relation to the present disclosure are omitted.

It should be emphasized that a term "include/comprise" when used herein refers to presence of features, elements, steps or components, but does not exclude presence or addition of one or more other features, elements, steps or components.

Herein, it should also be noted that, unless otherwise specified, a term "connection" herein may refer not only to a direct connection, but also to an indirect connection with an intermediate.

The embodiments of the present disclosure will be described below with reference to the accompanying drawings. Moreover, throughout the drawings, same or similar elements or same or similar steps are denoted by same reference numerals.

In order to overcome a problem of an existing emotion recognition method based on emotion measurement, the present disclosure provides a method and a system for evaluating and optimizing user experience in human-computer interaction, and a storage medium.

FIG. 1 is a schematic diagram of a method for evaluating and optimizing user experience in human-computer interaction according to an embodiment of the present disclosure. The method includes operations at steps S110 to S160.

At step S110, a multimodal biological signal of a user during a human-computer interaction process is obtained. The multimodal biological signal at least includes eye movement data.

It can be understood that the multimodal biological signal used in the embodiments of the present disclosure at least includes eye movement data. In order to further improve comprehensiveness and reliability of index parameters of a plurality of dimensions, in one or more embodiments of the present disclosure, the multimodal biological signal may further include at least one of the biological signal data such as physiological data, electroencephalographic data, brain imaging data, or behavioral data. The plurality of dimensions at least includes one or a combination of fatigue degree dimension, emotional state dimension, or cognitive load dimension.

At step S120, the multimodal biological signal is preprocessed to extract a fixation position and index parameters of a plurality of dimensions at each time point. The fixation position is extracted based on an eye movement data feature corresponding to the eye movement data.

It can be understood that each dimension in the embodiments of the present disclosure may at least include the fatigue degree dimension, the emotional state dimension, or the cognitive load dimension to effectively improve the comprehensiveness of the index parameters of the plurality of dimensions, thereby improving reliability and effectiveness of subsequent acquisition of a user experience evaluation score.

In the step S120 of the embodiment of the present disclosure, the operation of the preprocessing the multimodal biological signal to extract the fixation position and the index parameters of the plurality of dimensions at each time point includes: 1) extracting, based on the eye movement data feature, a plurality of index parameters including fixation position, blink rate, and eyelid closure; 2) extracting, based on a physiological data feature, a plurality of index parameters including a serum creatinine SCR amplitude and an LF/HF value of a frequency-domain index, in which LF represents a low-frequency radiofrequency, and HF represents a high-frequency radiofrequency; and 3) extracting, based on a brain imaging data feature, a plurality of index parameters including an alpha asymmetry index, an $(\alpha+\theta)/\beta$ value of a frequency-domain index, and oxyhemoglobin parameter HbO2, in which $\alpha$, $\beta$, and $\theta$ represent a signal quantity within a given frequency band of an $\alpha$ wave, a signal quantity within a given frequency band of a $\beta$ wave, and a signal quantity within a given frequency band of a $\theta$ wave, respectively. The present disclosure is not limited thereto, and the above multidimensional parameter indexes are only examples. For example, they can further include extracting a time-domain index and a time-frequency index based on the electroencephalographic data. All the features that can be extracted from the multimodal biological signal and that can be easily thought of by those skilled in the art belong to the protection scope of the present disclosure.

Extracting an electroencephalographic time series feature includes extracting information such as kurtosis, skewness, mean, standard deviation, event-related potential, ERP latency, and ERP peak of an electroencephalographic signal mainly through mathematical statistics analysis in a time domain.

In a frequency domain, a Fourier transform, Welch, a multi-window method, an autoregressive model, etc., are mainly used to analyze energy values of electroencephalography in five frequency bands of Delta, Theta, Alpha, Beta, and Gamma, as well as brain cognitive function indexes such as $\alpha/\beta$, $\theta/\beta$, $(\alpha+\theta)/\beta$, $(\alpha+\theta)/(\alpha+B)$, $\theta/(\alpha+B)$, SMR (db). Nonlinear dynamic analysis includes complexity, entropy, Lyapunov index, etc. The complexity index includes Lempel-Ziv complexity, Lempel-Ziv sorting complexity, etc. The entropy index includes time domain-based Shannon entropy, approximate entropy, sample entropy, and sorting entropy, and time and frequency-based entropy includes wavelet entropy and Hilbert-Huang spectrum entropy.

A brain functional connectivity index is used to evaluate information connectivity between brain regions. Each part of a brain has its unique function in human behavior. A simplest task requires a plurality of brain regions to cooperate together. Commonly used indexes include a coherence-based index, a phase synchronization-based index, a generalized synchronization-based index, and a Granger causality-based index.

Extracting an electroencephalographic image feature primarily includes visualizing, based on a graph theory and an international 10-20 system, some indexes of the time domain and the brain functional connectivity, analyzing space-time information based on a CSP, constructing a 2D map, and may also construct a 3D dense connection network based on time feature, frequency feature, space feature, and other features. At step S130, the index parameters of each of the plurality of dimensions are standardized, and a user experience evaluation score of each dimension is obtained, based on each standardized index parameter of each dimension and a predetermined weight for each index parameter, by means of a weighted average.

The step of standardizing the index parameters of the plurality of dimensions is performed, and the values of the standardized index parameters of the plurality of dimensions include a positive value and a negative value. Further, the method further includes: normalizing the standardized index parameters of the plurality of dimensions. The values of the normalized index parameters of the plurality of dimensions include a positive value and a negative value.

In the step S130 of the embodiment of the present disclosure, the operation of obtaining, based on each standardized index parameter of each dimension and the predetermined weight for each index parameter, the user experience evaluation score of each dimension by means of the weighted average includes: 1) calculating, based on the blink rate and the eyelid closure and weights corresponding to the index parameters of the blink frequency and the eyelid closure, a user experience evaluation score of the fatigue degree dimension by means of the weighted average; 2) calculating a user experience evaluation score of the emotional state dimension by means of the weighted average and based on the serum creatinine SCR amplitude, the LF/HF value of the frequency-domain index, the alpha asymmetry index and weights corresponding to the index parameters of the serum creatinine SCR amplitude, the LF/HF value of the frequency-domain index and the alpha asymmetry index; and 3) calculating, based on $(\alpha+\theta)/\beta$ and the oxyhemoglobin saturation HbO2 and weights corresponding to the index parameters of $(\alpha+\theta)/\beta$ and the oxyhemoglobin saturation HbO2, a user experience evaluation score of the cognitive load dimension by means of the weighted average. The present disclosure is not limited to this, and the above dimensional division of index parameters is only an example. For example, the index parameters also include frequency domain indexes and time-frequency indexes based on electroencephalographic data to determine the user experience evaluation score of the user's emotional state dimension. Any user experience evaluation score that is calculated based on index parameters extracted from the multimodal biological signal and that can be easily thought of by technical personnel in this field belongs to the technical scope protected by the present disclosure.

In step S140 of the embodiment of the present disclosure, an operation of obtaining, based on each standardized index parameter of each dimension and a predetermined weight for each index parameter, a user experience evaluation score of each dimension by means of a weighted average is represented as a formula of:

$$N = \frac{\sum_{x=1}^{m} w_x V_x}{w_1 + w_2 + \ldots + w_m}$$

where: $w_x$ represents a weight for an x-th index parameter; $w_x$ represents an x-th standardized index parameter of a corresponding dimension; and N represents a user experience evaluation score of the corresponding dimension.

At step S140, based on the user experience evaluation score of each dimension and a predetermined weight for the user experience evaluation score, an overall user experience evaluation result is obtained by means of the weighted average.

In step S140 of the embodiment of the present disclosure, the operation of the obtaining, based on the user experience evaluation score of each dimension and the predetermined weight for the user experience evaluation score, the overall user experience evaluation result by means of the weighted average is represented as a formula of:

$$S = \frac{\sum_{i=1}^{n} W_i N_i}{W_1 + W_2 + \ldots + W_n}$$

where: $W_i$ represents a weight for a user experience evaluation score of an i-th dimension; $N_i$ represents the user experience evaluation score of the i-th dimension; and S represents an overall user experience evaluation result.

At step S150, user experience situation data of the user for a current fixation position on a human-computer interaction interface is visually presented based on the overall user experience evaluation result.

In step S150 of the embodiment of the present disclosure, the operation of the visually presenting, based on the overall user experience evaluation result, the user experience situation data of the user for the current fixation position on the human-computer interaction interface includes: labeling at least one of different colors or transparency levels for the current fixation location based on the overall user experience evaluation result. For example, if the overall user experience evaluation result is a positive value, the current fixation position is labeled with a black color, and the transparency level of the black color increases as the overall user experience evaluation result decreases; if the overall user experience evaluation result is a negative value, the current fixation position is labeled with a red color, and the transparency level of the red color decreases as the overall user experience evaluation result decreases. The present disclosure is not limited thereto, for example, a positive overall user experience evaluation result may be labeled with a red color, and a negative overall user experience evaluation result may be labeled with a green color. All simple modifications to technical features of the present disclosure belong to the protection scope of the present disclosure.

At step S160, a correction parameter is acquired based on at least one of the user experience evaluation score of the user for each dimension or the visually presented user experience situation data of the user for different fixation positions on the human-computer interaction interface, and a weight for each index parameter of each dimension and a weight for the user experience evaluation score of each dimension are optimized based on the correction parameter for a finite number of iterations using a machine learning optimization algorithm.

In the step S160 of the embodiment of the present disclosure, the operation of the acquiring the correction parameter based on the at least one of the user experience evaluation score of the user for each dimension or the visually presented user experience situation data of the user for the different fixation positions on the human-computer interaction interface includes: acquiring subjective questionnaire data of the user for a fatigue degree dimension, an emotional state dimension, and a cognitive load dimension, and calculating the correction parameter based on the subjective questionnaire data.

In the step S160 of the embodiment of the present disclosure, the operation of the acquiring the correction parameter based on the at least one of the user experience evaluation score of the user for each dimension or the visually presented user experience situation data of the user for the different fixation positions on the human-computer interaction interface further includes: acquiring a subjective score of the user for the visually presented user experience situation data of the different fixation positions on the human-computer interaction interface, and calculating the correction parameter based on the subjective score. The present disclosure is not limited to thereto, and subjective feedback of the user is diverse, for example, by filling in a pre-designed subjective questionnaire, asking questions about a score/rating of different regions/modules of the human-computer interaction interface, and calculating the correction parameter based on the above operations. The correction parameter may optionally be a normalized score for each fixation position/each region on the human-computer interaction interface.

In the step S160 of the embodiment of the present disclosure, the machine learning optimization algorithm is a Newton method or a gradient descent method.

In the step S160 of the embodiment of the present disclosure, the operation of the optimizing, based on the correction parameter, the weight for each index parameter of each dimension and the weight for the user experience evaluation score of each dimension for the finite number of iterations using the machine learning optimization algorithm includes: 1) building a machine learning optimization model by taking the weight for each index parameter of each dimension and the weight for the user experience evaluation score of each dimension as to-be-optimized parameters; 2) constructing a loss function based on the correction parameter; and 3) optimizing the machine learning optimization model for the finite number of iterations based on the loss function, and obtaining the optimized weight for each index parameter of each dimension and the optimized weight for the user experience evaluation score of each dimension.

Further, in some embodiments of the present disclosure, the method further includes, subsequent to the operation of the step S160: labeling, based on fixation positions at a plurality of historical time points and overall user experience evaluation results corresponding to the fixation positions, at least one of different colors or transparency levels for the different fixation positions on the human-computer interaction interface, and filling a blank region based on at least one of a color or transparency level of a fixation position around the blank region, to visually present the user experience situation of the user for different regions on the human-computer interaction interface.

In some other embodiments of the present disclosure, the method further includes, subsequent to the operation of the step S160: generating a user experience feedback report based on the visually presented user experience situation data of the current fixation position on the human-computer interaction interface, the user experience feedback report including user experience feedback reports generated for different partitions based on predetermined partitions on the human-computer interaction interface.

In some embodiments of the present disclosure, the operation of the obtaining, based on each standardized index parameter of each dimension and a predetermined weight for each index parameter, a user experience evaluation score of each dimension by means of a weighted average is represented as a formula of:

$$N = \frac{\sum_{x=1}^{m} w_x V_x}{w_1 + w_2 + \ldots + w_m}$$

where: $w_x$ represents a weight for an x-th index parameter; $w_x$ represents an x-th standardized index parameter of a corresponding dimension; and N represents a user experience evaluation score of the corresponding dimension.

The operation of the obtaining, based on the user experience evaluation score of each dimension and the predetermined weight for the user experience evaluation score, the overall user experience evaluation result by means of the weighted average is represented as a formula of:

$$S = \frac{\sum_{i=1}^{n} W_i N_i}{W_1 + W_2 + \ldots + W_n}$$

where: $W_i$ represents a weight for a user experience evaluation score of an i-th dimension; $N_i$ represents the user experience evaluation score of the i-th dimension; and S represents an overall user experience evaluation result.

In one embodiment of the present disclosure, the evaluation results of at least three dimensions of cognitive compliance, emotional state, or fatigue degree are obtained based on the extracted index parameters and combined with a data processing and analysis algorithm, and weighted calculation is further performed to obtain the user experience level evaluation.

1) The emotional state (E) includes an emotional valence (V) and an emotional arousal level (M).

(1) The emotional valence (V) is calculated based on a ΔPAI index of a frontal lobe alpha asymmetry index of EEG, ΔPAI is a positive value (avoidance tendency), or ΔPAI is a negative value (approach tendency). The frontal lobe alpha asymmetry index (PAI index) is equal to a logarithmic power of a left frontal AF3 electrode minus a logarithmic power of a right frontal AF4, and then divided by a sum of the logarithmic power of the left frontal AF3 electrode and the logarithmic power of the right frontal AF4. A PAI index of the sampling point is subtracted from a PAI index of a previous sampling point to obtain a baseline-free ΔPAI index.

$$V = \Delta PAI =$$

$$PAI_n - PAI_{n-1} = \left(\frac{\log(AF3)_n - \log(AF4)_n}{\log(AF3)_n + \log(AF4)_n}\right) - \left(\frac{\log(AF3)_{n-1} - \log(AF4)_{n-1}}{\log(AF3)_{n-1} + \log(AF4)_{n-1}}\right)$$

where n represents a measurement result of a sampling point at a current time point, and n−1 represents a measurement result of the sampling point at a previous time point.

(2) A score of the emotional arousal level (M) is based on the SC amplitude and the LF/HF value. After the two indexes are normalized, a weighted average thereof is assigned to the emotional arousal level. The emotional arousal level is better when the score is a higher value. Weights of the two indexes are 50% each. The normalization method is: a value of a current sampling point minus a value of a previous sampling point.

$$M = 0.5 * \left[(SC_n - SC_{n-1}) + \left(LF/HF_n - LF/HF_{n-1}\right)\right]$$

(3) A formula for calculating the emotional state is represented as: E=V*M

2) A score of a cognitive load (W) is obtained by a frequency-domain index $(\alpha+\theta)/\beta$ of the electroencephalogram (EEG), and after the index is normalized, the value is assigned to the cognitive load. The normalization method is: a value of a current sampling point minus a value of a previous sampling point, and a calculation formula thereof is represented as: W=[$(\alpha+\theta)/\beta$]n−[$(\alpha+\theta)/\beta$](n−1).

3) A score of a fatigue degree (F) is obtained by eyelid closure (P) and blink rate (B), and after the indexes are normalized, a weighted average is assigned to the fatigue degree. The normalization method is: a value of a current sampling point minus a value of a previous sampling point. The eyelid closure index has a weight of 70%, and the blink rate has a weight of 30%. A calculation formula thereof is represented as: F=0.7*ΔP+0.3*ΔB.

4) A score of a user experience level(S) is obtained by a weighted average of the scores of the three dimensions. The emotional state has a weight of 50%, the cognitive load has a weight of 30%, and the fatigue level has a weight of 20%. The user experience level deteriorates when the S value increases, and vice versa. A calculation formula thereof is represented as: S=0.5*E−0.3*W+0.2*F.

In the above disclosed embodiment, the operation of the preprocessing the multimodal biological signal to extract the fixation position and the index parameters of the plurality of dimensions at each time point includes: 1) extracting, based on the eye movement data feature, a plurality of index parameters including fixation position, blink rate, and eyelid closure; 2) extracting, based on a corresponding physiological data feature, a plurality of index parameters including a serum creatinine SCR amplitude and an LF/HF value of a frequency-domain index, in which LF represents a low-frequency radiofrequency, and HF represents a high-frequency radiofrequency; and 3) extracting, based on a corresponding brain imaging data feature, a plurality of index parameters including an alpha asymmetry index, an $(\alpha+\theta)/\beta$ value of a frequency-domain index, and oxyhemoglobin saturation HbO2, in which $\alpha$, $\beta$, and $\theta$ represent a signal quantity within a given frequency band of an $\alpha$ wave, a signal quantity within a given frequency band of a $\beta$ wave, and a signal quantity within a given frequency band of a $\theta$ wave, respectively. The present disclosure is not limited thereto, and the above multidimensional parameter indexes are only examples. For example, the parameter index characterizing the emotional state further includes SC. All the features that can be extracted from the multimodal biological signal and that can be easily thought of by those skilled in the art belong to the protection scope of the present disclosure.

In some embodiments of the present disclosure, the index parameter is also referred as to a characteristic index or a characteristic parameter. A characteristic index characterizing the emotional state includes but is not limited to: a frontal lobe alpha asymmetry index obtained based on the electroencephalogram (EEG), serum creatinine SCR amplitude, and LF/HF; a characteristic index characterizing the cognitive load includes but is not limited to: a electroencephalogram-based frequency-domain index $(\alpha+\theta)/\beta$ and an HbO2 concentration obtained based on functional near-infrared spectroscopy (fNIRS); a characteristic index characterizing the fatigue degree includes but is not limited to: eyelid closure and blink rate. $\alpha$, $\beta$, and $\theta$ represent an $\alpha$ wave, a $\beta$ wave, and a $\theta$ wave, respectively. The frequency-domain index $(\alpha+\theta)/\beta$ represents a ratio of the electroencephalogram in different frequency domains, which is configured to reflect a speed of a change of the electroencephalographic signal over time. LF/HF represents a ratio of a low-frequency domain (Low Frequency) to a high-frequency domain (High Frequency). LF/HF reflects a relative activity of a sympathetic nerve and a parasympathetic nerve. The above content is only an example and does not limit the specific index parameters selected by the present disclosure.

FIG. 2 is a flowchart of a method for evaluating and optimizing user experience in human-computer interaction according to an embodiment of the present disclosure. First, collected multimodal data such as eye movement data, physiology data, and electroencephalography (imaging) data are preprocessed separately to extract an index parameter. Features extracted based on the eye movement data include but are not limited to: fixation position, blink rate, and eyelid closure; features extracted based on the physiological data include but are not limited to: time-domain index SCR amplitude and pulse-frequency-domain index LF/HF; features extracted based on the brain imaging data include but are not limited to: alpha asymmetry index and $(\alpha+\theta)/\beta$, near infrared index oxygenation, deoxygenation, and total hemoglobin concentration HbO2. Then, a user experience evaluation score of a fatigue degree dimension is calculated based on the blink rate and the eyelid closure, a user experience evaluation score of the emotional state dimension is calculated based on the time-domain index SCR amplitude and the pulse-frequency-domain index LF/HF, and a user experience evaluation score of the cognitive compliance dimension is calculated based on the alpha asymmetry index, $(\alpha+\theta)/\beta$ and total hemoglobin concentration HbO2. Afterwards, an overall user experience evaluation result is calculated based on the user experience evaluation score of each dimension; at least one of a color or transparency level is labeled for different fixation positions on the human-computer interaction interface by combining the overall user experience evaluation result and the fixation position at a current time point, and each region is filled based on the at least one of the color or the transparency level labeled for the different fixation positions; and a weight coefficient of each index parameter of each dimension is optimized in combination with correction from the user.

In FIG. 2, the step of optimizing the weight coefficient of each index parameter of each dimension is an operation of optimizing the weight coefficient of each index parameter of each dimension using a learning algorithm (such as a Newton method or a gradient descent method).

Figure 3:
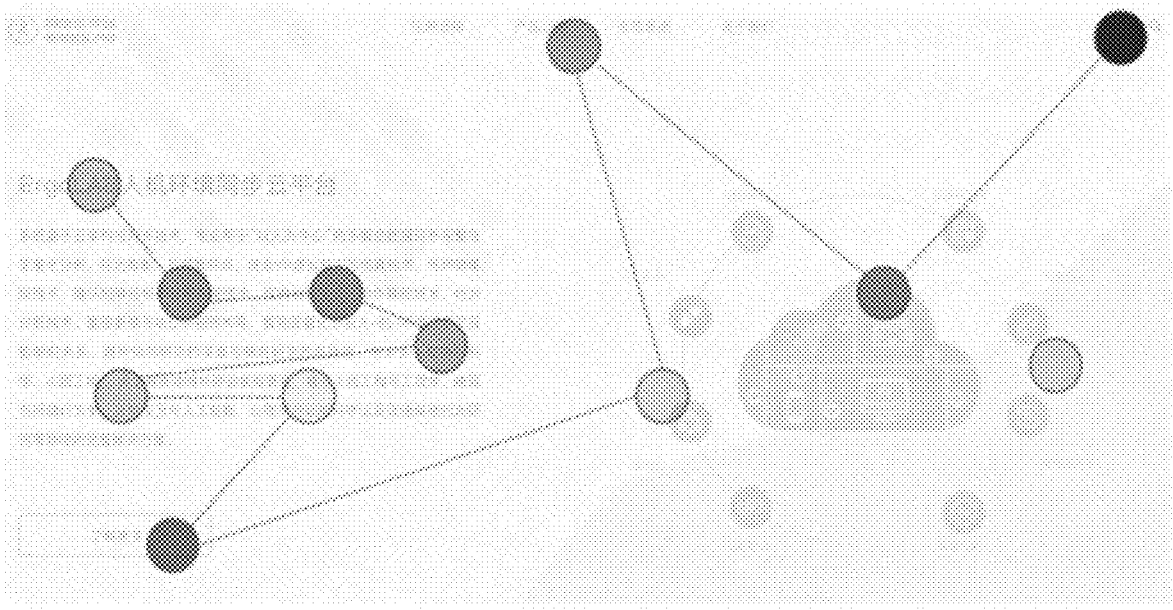
FIG. 3 is a schematic diagram of visually presenting user experience situation according to an embodiment of the present disclosure.

FIG. 3 is a schematic diagram of visually presenting user experience situation according to an embodiment of the present disclosure. In a specific embodiment of the present disclosure, the color and the transparency level are differentially labeled on the human-computer interaction interface based on the fixation position of the eye movement data and the calculated overall user experience evaluation result, and a calculated user experience level is displayed in real time. In one embodiment, a corresponding eye movement fixation is labeled with a color based on the user experience level calculated in real time. When S value (overall user experience evaluation result) is a positive value, the fixation has a black color. In this case, the transparency level of the black color increases as the value decreases. When the S value is a negative value, the fixation has a red color. In this case, the transparency level of the red color decreases as the value deceases. It should be explained that when the S value is the positive value, it indicates that the user's emotion is positive, otherwise, it indicates that the user's emotion is negative. In FIG. 3, a background content represents the human-computer interaction interface, and a text and a picture content thereof are only examples and have no actual meaning. Each circular region represents a fixation, and a dotted line represents the fixation movement order. The color (FIG. 3 is a color image before grayscale processing) and the transparency level of each circular region represent positive or negative and a size of the S value, respectively.

Figure 4:
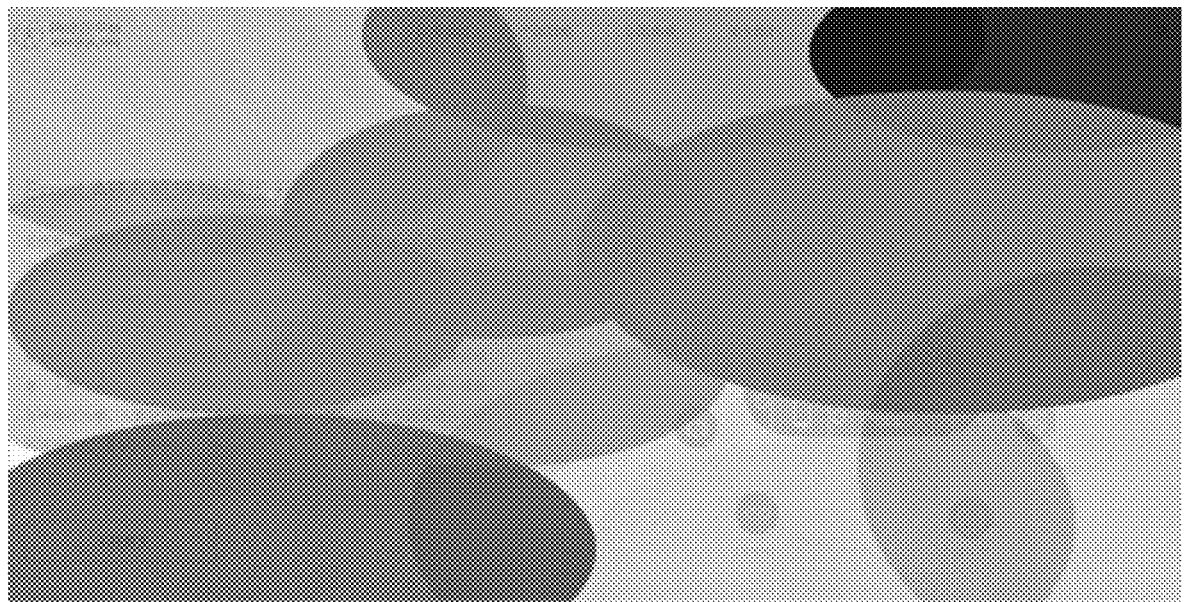
FIG. 4 is a schematic diagram of visually presenting user experience situation with filling according to an embodiment of the present disclosure.

FIG. 4 is a schematic diagram of visually presenting user experience situation with filling according to an embodiment of the present disclosure. In a specific embodiment of the present disclosure, a blank region is filled with color (the filling method includes but is not limited to copying) based on colors of eye movement fixations around the blank region, the colors of the eye movement fixations are arranged in levels to display the corresponding human-computer interface regions, i.e., the experience situations of the different regions on the human-computer interaction interface. As illustrated in FIG. 4, a region around the fixation is filled based on a color and transparency level of the fixation, to form the displayed effect in FIG. 4. Ellipses in FIG. 4 are regions of different colors (colored before grayscale processing) and different transparency levels, indicating the experience evaluation of the user for the region. Similarly, a background content in FIG. 3 represents the human-computer interaction interface, and a text and a picture content thereof are only examples and have no actual meaning.

In an embodiment of the present disclosure, the method further includes acquiring an interface region ranking modified based on self-experience of the user.

In an embodiment of the present disclosure, the method further includes acquiring a color transparency level of the interface region modified based on the self-experience of the user. The region using the fixation color is uniformly changed when modified.

In an embodiment of the present disclosure, the method further includes: identifying a fatigue degree of the user based on the fatigue degree dimension in a vehicle driving scene; issuing a warning message on the human-computer interaction interface to remind the user to rest; and issuing, when a plurality of reminders is invalid, an automatic alarm.

In the method for evaluating and optimizing user experience in human-computer interaction according to the present disclosure, the user experience of each fixation/region on the human-computer interaction interface is identified based on the multimodal biological signal; in combination with the data processing and analysis algorithm, the product evaluation report is actively fed back based on the identification result, and the recognition accuracy is optimized in combination with the machine learning. Based on this evaluation method, designers can be assisted in optimizing the design of the human-computer interaction interface, improving the design scheme, and thus improving the user experience level of the product. As described above, the present disclosure provides a real-time, comprehensive, and accurate method for evaluating user experience in human-computer interaction.

The fixation position and the index parameters of the plurality of dimensions can be extracted based on the multimodal biological signal feature; the weighted calculation is performed based on the index parameters of the plurality of dimensions to obtain the objective and accurate user experience evaluation result, and the fixation position is associated with the user experience evaluation result; the experience situation of the user for the different regions on the human-computer interaction interface can be further obtained; and the user experience in the human-computer interaction can be automatically and real-timely evaluated based on the richer data.

Correspondingly to the above-mentioned method, the present disclosure further provides a system for evaluating and optimizing user experience in human-computer interaction. The system includes a computer device. The computer device includes a processor and a memory. The memory has computer instructions stored therein. The processor is configured to execute the computer instructions stored in the memory. The system, when the computer instructions are executed by the processor, performs the steps of the method as described above.

Embodiments of the present disclosure further provide a computer-readable storage medium. The computer-readable storage medium has a computer program stored thereon. The computer program, when executed by a processor, implements the steps of the method as described above. The computer-readable storage medium can be a tangible storage medium, such as a Random Access Memory (RAM), a memory, a Read-Only Memory (ROM), an Electrically Programmable ROM, an Electrically Erasable Programmable Read-Only Memory, a register, a floppy disk, a hard disk, a removable storage disk, a CD-ROM, or any other form of storage medium known in the technical field.

Those of ordinary skill in the art should understand that the exemplary components, systems, and methods described in combination with the embodiments disclosed herein can be implemented in hardware, software or a combination thereof. Whether these functions are executed by hardware or software is dependent on particular use and design constraints of the technical solutions. Professional technicians may use different methods to implement the described functions for each specific application, but such implementation should not be considered to be beyond the scope of the present disclosure. When implemented in hardware, it may be, for example, an electronic circuit, an Application-Specific Integrated Circuit (ASIC), appropriate firmware, a plug-in, a function card, etc. When implemented in software, the elements of the present disclosure are programs or code segments configured to perform the required tasks. The program or code segment may be stored in a machine-readable medium, or transmitted on a transmission medium or a communication link via a data signal carried in a carrier wave.

It should be clear that the present disclosure is not limited to the specific configurations and processes described above and shown in the figures. For sake of simplicity, a detailed description of the known methods is omitted herein. In the above-mentioned embodiments, the several specific steps are described and shown as examples. However, the method process of the present disclosure is not limited to the specific steps described and shown, and those skilled in the art may make various changes, modifications, and additions, or change the order between the steps after understanding the spirit of the present disclosure.

In the present disclosure, features described and/or illustrated for one embodiment may be used in the same way or in a similar way in one or more other embodiments, and/or combined with features of other embodiments or replace features of other embodiments.

While the embodiments of the present disclosure have been described above, they are not intended to limit the present disclosure. For those skilled in the art, various changes and variations can be made to the embodiments of the present disclosure. Any modifications, equivalent substitutions, and improvements made within the spirit and principle of the present disclosure are to be encompassed by the protection scope of the present disclosure.

What is claimed is:

1. A method for evaluating and optimizing user experience in human-computer interaction, the method comprising:

acquiring a multimodal biological signal of a user during a human-computer interaction process, the multimodal biological signal at least comprising eye movement data;

preprocessing the multimodal biological signal to extract a fixation position and index parameters of a plurality of dimensions at each time point, the fixation position being extracted based on an eye movement data feature corresponding to the eye movement data;

standardizing the index parameters of each of the plurality of dimensions, and obtaining, based on each standardized index parameter of each dimension and a predetermined weight for each index parameter, a user experience evaluation score of each dimension by means of a weighted average;

obtaining, based on the user experience evaluation score of each dimension and a predetermined weight for the user experience evaluation score, an overall user experience evaluation result by means of the weighted average, and associating the overall user experience evaluation result with the fixation position;

visually presenting, based on the overall user experience evaluation result associated with the fixation position, user experience situation data of the user for a current fixation position on a human-computer interaction interface; and acquiring a correction parameter based on at least one of the user experience evaluation score of the user for each dimension or the visually presented user experience situation data of the user for different fixation positions on the human-computer interaction interface, and optimizing, based on the correction parameter, a weight for each index parameter of each dimension and a weight for the user experience evaluation score of each dimension for a finite number of iterations using a machine learning optimization algorithm, wherein

16 the multimodal biological signal further comprises one or a combination of physiological data, electroencephalographic data, brain imaging data, or behavioral data; and the plurality of dimensions at least comprises one or a combination of a fatigue degree dimension, an emotional state dimension, or a cognitive load dimension.

2. The method for evaluating and optimizing user experience in human-computer interaction according to claim 1, wherein said preprocessing the multimodal biological signal to extract the fixation position and the index parameters of the plurality of dimensions at each time point comprises:

extracting, based on the eye movement data feature, a plurality of index parameters comprising fixation position, blink rate, and eyelid closure;

extracting, based on a corresponding physiological data feature, a plurality of index parameters comprising a serum creatinine SCR amplitude and an LF/HF value of a frequency-domain index, wherein LF represents a low-frequency radiofrequency, and HF represents a high-frequency radiofrequency; and extracting, based on a corresponding brain imaging data feature, a plurality of index parameters comprising an alpha asymmetry index, an $(\alpha+\theta)/\beta$ value of a frequency-domain index, and oxyhemoglobin saturation HbO2, wherein $\alpha$, $\beta$, and $\theta$ represent a signal quantity within a given frequency band of an $\alpha$ wave, a signal quantity within a given frequency band of a $\beta$ wave, and a signal quantity within a given frequency band of a $\theta$ wave, respectively.

3. The method for evaluating and optimizing user experience in human-computer interaction according to claim 2, wherein said obtaining, based on each standardized index parameter of each dimension and the predetermined weight for each index parameter, the user experience evaluation score of each dimension by means of the weighted average comprises:

calculating, based on the blink rate and the eyelid closure and weights corresponding to the index parameters of the blink frequency and the eyelid closure, a user experience evaluation score of the fatigue degree dimension by means of the weighted average;

calculating, based on the serum creatinine SCR amplitude and the LF/HF value of the frequency-domain index and weights corresponding to the index parameters of the serum creatinine SCR amplitude and the LF/HF value of the frequency-domain index, a user experience evaluation score of the emotional state dimension by means of the weighted average; and calculating a user experience evaluation score of the cognitive load dimension by means of the weighted average and based on the alpha asymmetry index, the $(\alpha+\theta)/\beta$ value of the frequency-domain index, the oxyhemoglobin saturation HbO2, and weights corresponding to the index parameters of the alpha asymmetry index, the $(\alpha+\theta)/\beta$ value of the frequency-domain index, and the oxyhemoglobin saturation HbO2.

4. The method for evaluating and optimizing user experience in human-computer interaction according to claim 1, wherein values of the standardized index parameters comprise a positive value and a negative value; and the method for evaluating and optimizing user experience in human-computer interaction further comprises: normalizing the standardized index parameters of the plurality of dimensions, values of the normalized index parameters of the plurality of dimensions comprising a positive value and a negative value.

5. The method for evaluating and optimizing user experience in human-computer interaction according to claim 1, wherein the machine learning optimization algorithm is a Newton method or a gradient descent method; and said optimizing, based on the correction parameter, the weight for each index parameter of each dimension and the weight for the user experience evaluation score of each dimension for the finite number of iterations using the machine learning optimization algorithm comprises:

building a machine learning optimization model by taking the weight for each index parameter of each dimension and the weight for the user experience evaluation score of each dimension as to-be-optimized parameters;

constructing a loss function based on the correction parameter; and optimizing the machine learning optimization model for the finite number of iterations based on the loss function, and obtaining the optimized weight for each index parameter of each dimension and the optimized weight for the user experience evaluation score of each dimension.

6. The method for evaluating and optimizing user experience in human-computer interaction according to claim 1, wherein said visually presenting, based on the overall user experience evaluation result associated with the fixation position, the user experience situation data of the user for the current fixation position on the human-computer interaction interface comprises:

labeling at least one of different colors or transparency levels for the current fixation location based on the overall user experience evaluation result associated with the fixation position.

7. The method for evaluating and optimizing user experience in human-computer interaction according to claim 1, wherein said acquiring the correction parameter based on the at least one of the user experience evaluation score of the user for each dimension or the visually presented user experience situation data of the user for the different fixation positions on the human-computer interaction interface comprises:

acquiring subjective questionnaire data of the user for a fatigue degree dimension, an emotional state dimension, and a cognitive load dimension, and calculating the correction parameter based on the subjective questionnaire data.

8. The method for evaluating and optimizing user experience in human-computer interaction according to claim 1, wherein said acquiring the correction parameter based on the at least one of the user experience evaluation score of the user for each dimension or the visually presented user experience situation data of the user for the different fixation positions on the human-computer interaction interface comprises:

acquiring a subjective score of the user for the visually presented user experience situation of the different fixation positions on the human-computer interaction interface, and calculating the correction parameter based on the subjective score.

9. The method for evaluating and optimizing user experience in human-computer interaction according to claim 1, further comprising:

labeling, based on fixation positions at a plurality of historical time points and overall user experience evaluation results corresponding to the fixation positions, at least one of different colors or transparency levels for the different fixation positions on the human-computer interaction interface, and filling a blank region based on at least one of a color or transparency level of a fixation position around the blank region, to visually present the user experience situation data of the user for different regions on the human-computer interaction interface.

10. The method for evaluating and optimizing user experience in human-computer interaction according to claim 1, further comprising:

generating a user experience feedback report based on the visually presented user experience situation data of the user for the current fixation position on the human-computer interaction interface, the user experience feedback report comprising user experience feedback reports generated for different partitions based on predetermined partitions on the human-computer interaction interface.

11. A system for evaluating and optimizing user experience in human-computer interaction, comprising:

a processor; and a memory having computer instructions stored therein, wherein the processor is configured to execute the computer instructions stored in the memory, and the system, when the computer instructions are executed by the processor, implements a method for evaluating and optimizing user experience in human-computer interaction, the method comprising:

acquiring a multimodal biological signal of a user during a human-computer interaction process, the multimodal biological signal at least comprising eye movement data;

preprocessing the multimodal biological signal to extract a fixation position and index parameters of a plurality of dimensions at each time point, the fixation position being extracted based on an eye movement data feature corresponding to the eye movement data;

standardizing the index parameters of each of the plurality of dimensions, and obtaining, based on each standardized index parameter of each dimension and a predetermined weight for each index parameter, a user experience evaluation score of each dimension by means of a weighted average;

obtaining, based on the user experience evaluation score of each dimension and a predetermined weight for the user experience evaluation score, an overall user experience evaluation result by means of the weighted average, and associating the overall user experience evaluation result with the fixation position;

visually presenting, based on the overall user experience evaluation result associated with the fixation position, user experience situation data of the user for a current fixation position on a human-computer interaction interface; and acquiring a correction parameter based on at least one of the user experience evaluation score of the user for each dimension or the visually presented user experience situation data of the user for different fixation positions on the human-computer interaction interface, and optimizing, based on the correction parameter, a weight for each index parameter of each dimension and a weight for the user experience evaluation score of each dimension for a finite number of iterations using a machine learning optimization algorithm, wherein the multimodal biological signal further comprises one or a combination of physiological data, electroencephalographic data, brain imaging data, or behavioral data; and the plurality of dimensions at least comprises one or a combination of a fatigue degree dimension, an emotional state dimension, or a cognitive load dimension.

12. The system for evaluating and optimizing user experience in human-computer interaction according to claim 11, wherein the system, when the computer instructions are executed by the processor, implementing an operation of preprocessing the multimodal biological signal to extract the fixation position and the index parameters of the plurality of dimensions at each time point comprises:

extracting, based on the eye movement data feature, a plurality of index parameters comprising fixation position, blink rate, and eyelid closure;

extracting, based on a corresponding physiological data feature, a plurality of index parameters comprising a serum creatinine SCR amplitude and an LF/HF value of a frequency-domain index, wherein LF represents a low-frequency radiofrequency, and HF represents a high-frequency radiofrequency; and extracting, based on a corresponding brain imaging data feature, a plurality of index parameters comprising an alpha asymmetry index, an $(\alpha+\theta)/\beta$ value of a frequency-domain index, and oxyhemoglobin saturation HbO2, wherein $\alpha$, $\beta$, and $\theta$ represent a signal quantity within a given frequency band of an $\alpha$ wave, a signal quantity within a given frequency band of a $\beta$ wave, and a signal quantity within a given frequency band of a $\theta$ wave, respectively.

13. The system for evaluating and optimizing user experience in human-computer interaction according to claim 12, wherein the system, when the computer instructions are executed by the processor, implementing an operation of obtaining, based on each standardized index parameter of each dimension and the predetermined weight for each index parameter, the user experience evaluation score of each dimension by means of the weighted average comprises:

calculating, based on the blink rate and the eyelid closure and weights corresponding to the index parameters of the blink frequency and the eyelid closure, a user experience evaluation score of the fatigue degree dimension by means of the weighted average;

calculating, based on the serum creatinine SCR amplitude and the LF/HF value of the frequency-domain index and weights corresponding to the index parameters of the serum creatinine SCR amplitude and the LF/HF value of the frequency-domain index, a user experience evaluation score of the emotional state dimension by means of the weighted average; and calculating a user experience evaluation score of the cognitive load dimension by means of the weighted average and based on the alpha asymmetry index, the $(\alpha+\theta)/\beta$ value of the frequency-domain index, the oxyhemoglobin saturation HbO2, and weights corresponding to the index parameters of the alpha asymmetry index, the $(\alpha+\theta)/\beta$ value of the frequency-domain index, and the oxyhemoglobin saturation HbO2.

14. The system for evaluating and optimizing user experience in human-computer interaction according to claim 11, wherein values of the standardized index parameters comprise a positive value and a negative value; and the system, when the computer instructions are executed by the processor, further implements: normalizing the standardized index parameters of the plurality of dimensions, values of the normalized index parameters of the plurality of dimensions comprising a positive value and a negative value.

15. The system for evaluating and optimizing user experience in human-computer interaction according to claim 11, wherein the machine learning optimization algorithm is a Newton method or a gradient descent method; and the system, when the computer instructions are executed by the processor, implementing an operation of optimizing, based on the correction parameter, the weight for each index parameter of each dimension and the weight for the user experience evaluation score of each dimension for the finite number of iterations using the machine learning optimization algorithm comprises:

building a machine learning optimization model by taking the weight for each index parameter of each dimension and the weight for the user experience evaluation score of each dimension as to-be-optimized parameters;

constructing a loss function based on the correction parameter; and optimizing the machine learning optimization model for the finite number of iterations based on the loss function, and obtaining the optimized weight for each index parameter of each dimension and the optimized weight for the user experience evaluation score of each dimension.

16. The system for evaluating and optimizing user experience in human-computer interaction according to claim 11, wherein the system, when the computer instructions are executed by the processor, implementing an operation of visually presenting, based on the overall user experience evaluation result associated with the fixation position, the user experience situation data of the user for the current fixation position on the human-computer interaction interface comprises:

labeling at least one of different colors or transparency levels for the current fixation location based on the overall user experience evaluation result associated with the fixation positions.

17. The system for evaluating and optimizing user experience in human-computer interaction according to claim 11, wherein the system, when the computer instructions are executed by the processor, implementing an operation of acquiring the correction parameter based on the at least one of the user experience evaluation score of the user for each dimension or the visually presented user experience situation data of the user for the different fixation positions on the human-computer interaction interface comprises:

acquiring subjective questionnaire data of the user for a fatigue degree dimension, an emotional state dimension, and a cognitive load dimension, and calculating the correction parameter based on the subjective questionnaire data.

18. A non-transient computer-readable storage medium, having a computer program stored thereon, wherein the computer program, when executed by a processor, implements a method for evaluating and optimizing user experience in human-computer interaction, the method comprising:

acquiring a multimodal biological signal of a user during a human-computer interaction process, the multimodal biological signal at least comprising eye movement data;

preprocessing the multimodal biological signal to extract a fixation position and index parameters of a plurality of dimensions at each time point, the fixation position being extracted based on an eye movement data feature corresponding to the eye movement data;

standardizing the index parameters of each of the plurality of dimensions, and obtaining, based on each standardized index parameter of each dimension and a predetermined weight for each index parameter, a user experience evaluation score of each dimension by means of a weighted average;

obtaining, based on the user experience evaluation score of each dimension and a predetermined weight for the user experience evaluation score, an overall user experience evaluation result by means of the weighted average, and associating the overall user experience evaluation result with the fixation position;

visually presenting, based on the overall user experience evaluation result associated with the fixation position, user experience situation data of the user for a current fixation position on a human-computer interaction interface; and acquiring a correction parameter based on at least one of the user experience evaluation score of the user for each dimension or the visually presented user experience situation data of the user for different fixation positions on the human-computer interaction interface, and optimizing, based on the correction parameter, a weight for each index parameter of each dimension and a weight for the user experience evaluation score of each dimension for a finite number of iterations using a machine learning optimization algorithm, wherein the multimodal biological signal further comprises one or a combination of physiological data, electroencephalographic data, brain imaging data, or behavioral data; and the plurality of dimensions at least comprises one or a combination of a fatigue degree dimension, an emotional state dimension, or a cognitive load dimension.

\* \* \* \* \*